United States Patent [19]

Desai

[11] Patent Number: 5,395,312
[45] Date of Patent: Mar. 7, 1995

[54] SURGICAL TOOL

[76] Inventor: Ashvin Desai, 2338 Walsh Ave., Santa Clara, Calif. 95051

[21] Appl. No.: 60,576

[22] Filed: May 10, 1993

Related U.S. Application Data

[63] Continuation-in-part of Ser. No. 25,003, Mar. 2, 1993, which is a continuation-in-part of Ser. No. 779,108, Oct. 18, 1991, Pat. No. 5,322,503.

[51] Int. Cl.⁶ .............................................. A61M 1/00
[52] U.S. Cl. ...................................... 604/22; 604/30; 604/152; 606/39; 606/45
[58] Field of Search .................... 604/21, 22, 30, 33, 604/34, 35, 151, 152, 153, 902; 606/39, 40, 41, 45, 46, 47, 159, 171

[56] References Cited

U.S. PATENT DOCUMENTS

| | | | |
|---|---|---|---|
| 2,484,059 | 10/1949 | Wallace | 606/46 |
| 3,561,429 | 2/1971 | Jewett | 606/171 |
| 4,246,902 | 1/1981 | Martinez | 604/22 |
| 4,274,409 | 6/1981 | Bush | 604/153 |
| 4,299,221 | 11/1981 | Phillips et al. | |
| 4,508,532 | 4/1985 | Drews et al. | 604/22 |
| 4,705,500 | 11/1987 | Reimels et al. | 604/22 |
| 4,817,599 | 4/1989 | Drews | 604/151 |
| 4,857,046 | 8/1989 | Stevens et al. | 604/22 |
| 4,936,845 | 6/1990 | Stevens | 604/22 |
| 4,982,739 | 1/1991 | Hemstreet et al. | 604/34 |
| 5,002,553 | 3/1991 | Shiber | 604/22 |
| 5,046,486 | 9/1991 | Grulke et al. | |
| 5,136,469 | 8/1992 | Carusillo et al. | |
| 5,230,704 | 7/1993 | Moberg et al. | 604/35 |
| 5,261,883 | 11/1993 | Hood et al. | 604/30 |

FOREIGN PATENT DOCUMENTS

| | | | |
|---|---|---|---|
| 617857 | 6/1980 | Switzerland | 604/151 |
| 2063674 | 6/1981 | United Kingdom | 604/30 |
| 1602277 | 11/1981 | United Kingdom | 604/151 |

Primary Examiner—Ralph A. Lewis
Attorney, Agent, or Firm—David H. Jaffer

[57] ABSTRACT

A handheld surgical instrument consists of a housing capable of being hand held and including a front end to which a surgical tool is mounted. The tool can be used for electrosurgery and includes a conduit for irrigating or evacuating an interior portion of the body of a patient. The instrument also includes a chamber for temporarily retaining irrigation fluid and from which the fluid can be supplied along the conduit to the body of the patient. Drive means mounted to the housing acts on the chamber to move fluid from the chamber along the conduit to the body of the patient. The instrument also includes a fluid supply for supplying irrigation fluid to the chamber. In operation, the drive means acts to alternately decrease and increase the volume of the chamber to alternately expel fluid from and draw fluid into it.

11 Claims, 6 Drawing Sheets

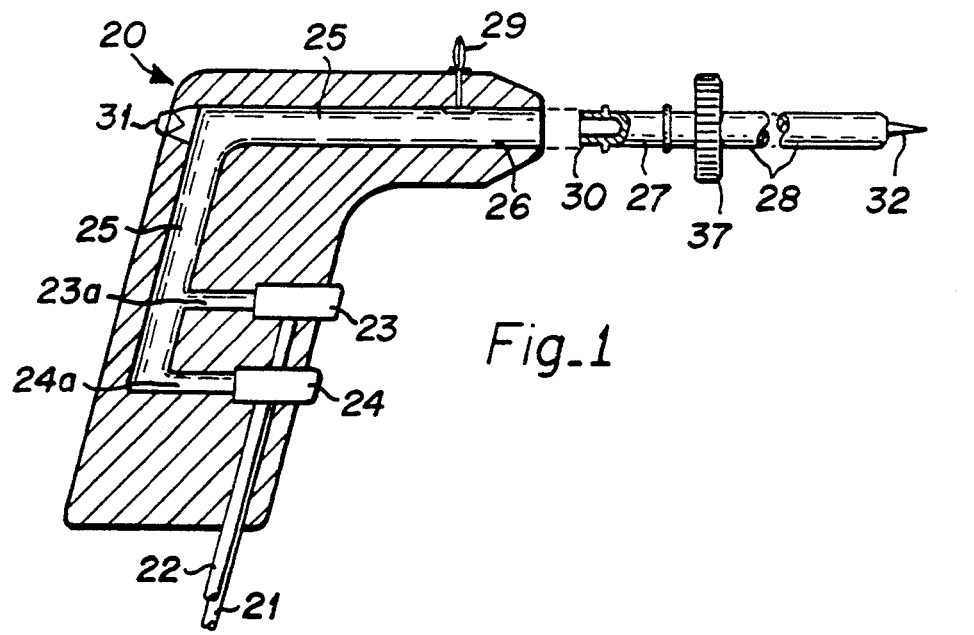
Fig_1
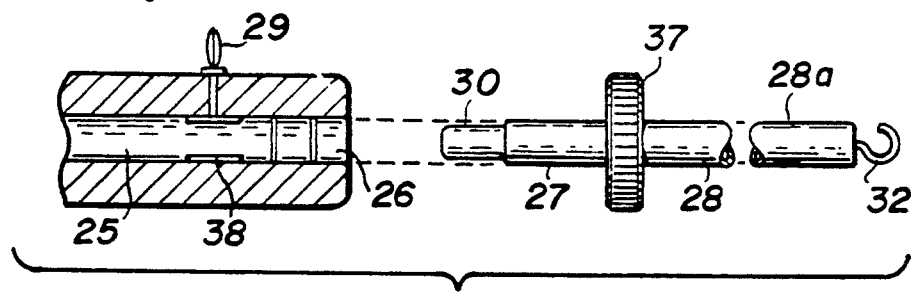
Fig_2
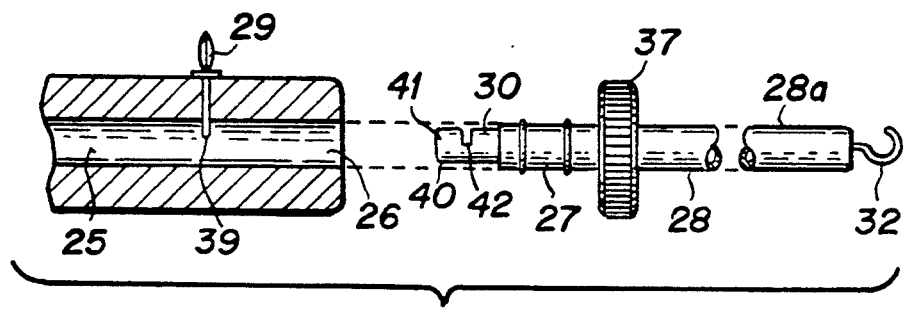
Fig_3
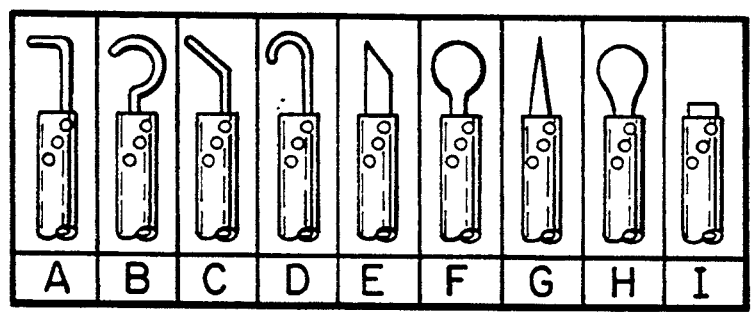
Fig_4

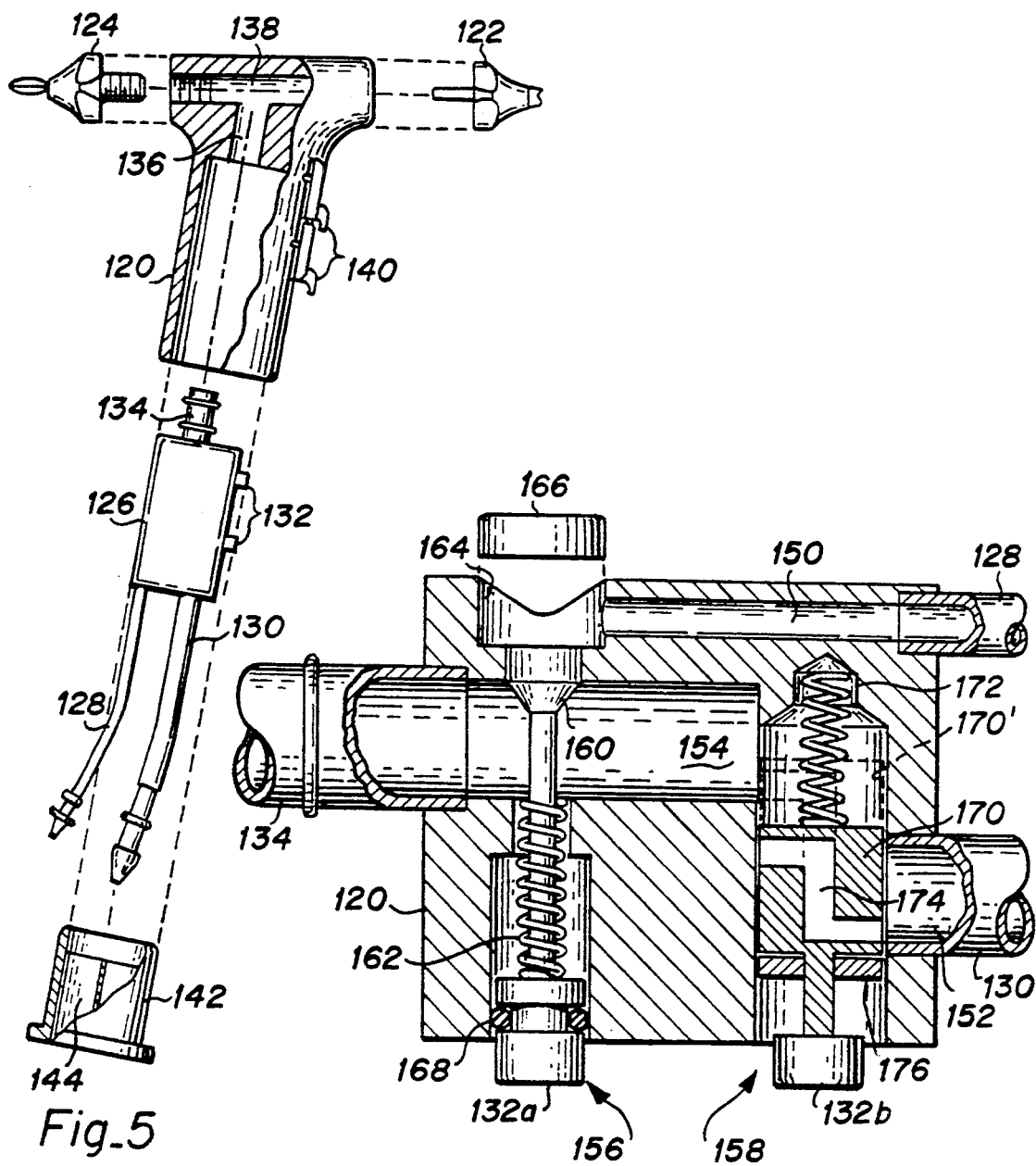
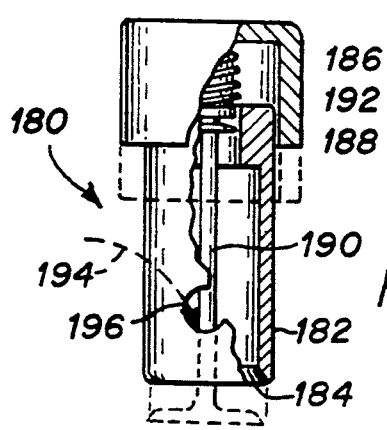
Fig_5  Fig_6  Fig_7

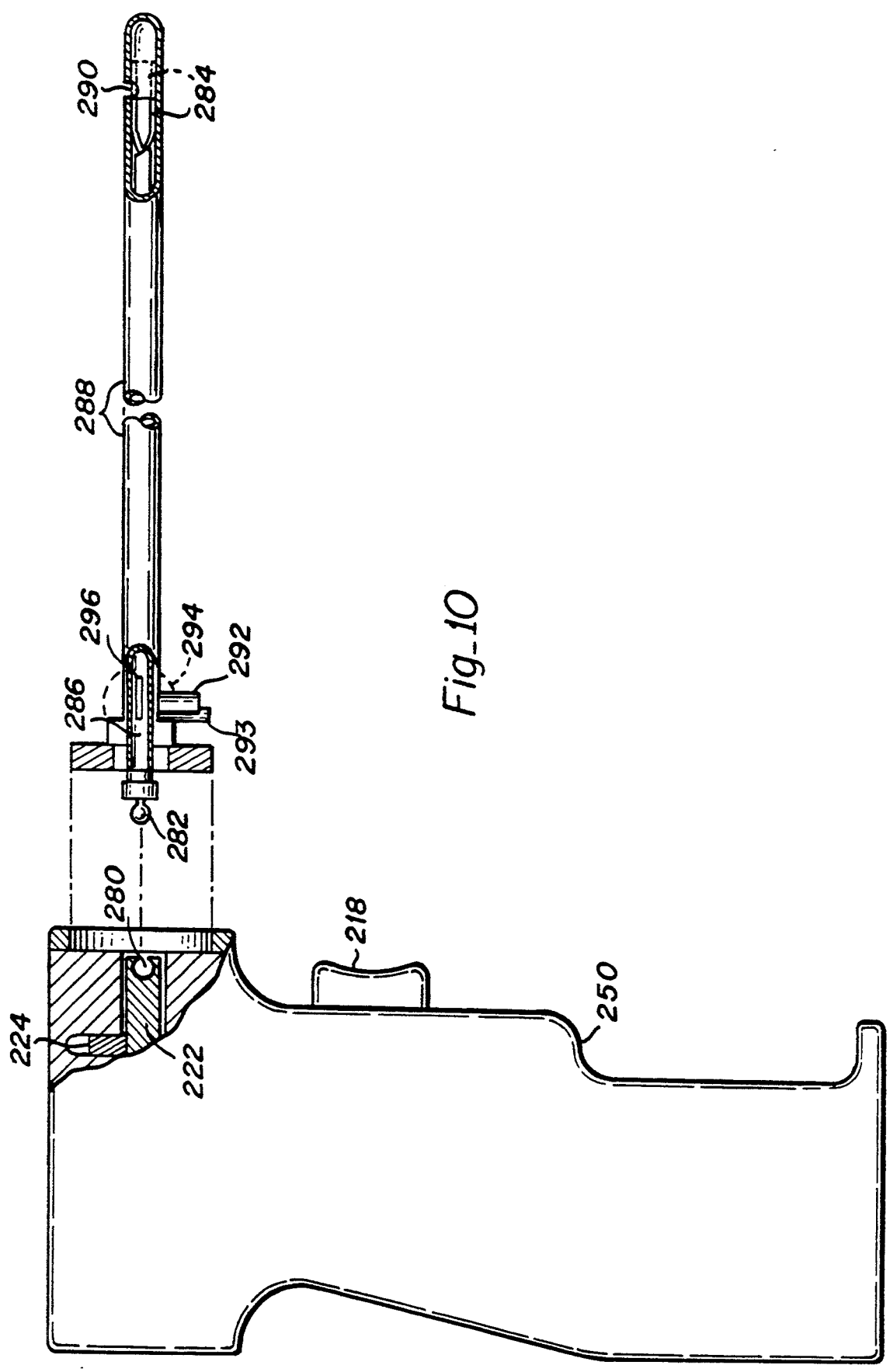

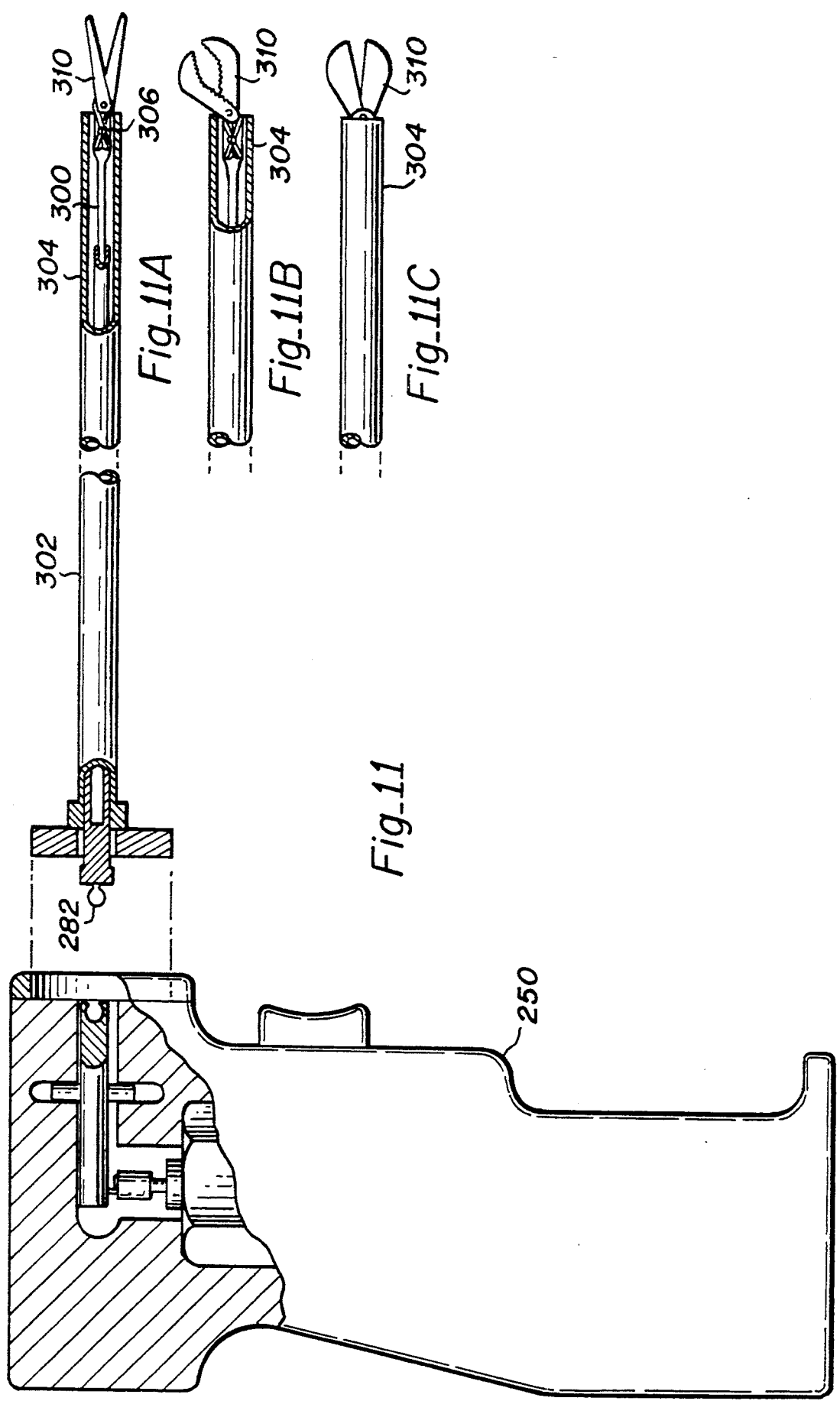

SURGICAL TOOL

RELATED CASES

This application is a continuation-in-part of the U.S. patent application Ser. No. 08/025,003, filed Mar. 2, 1993, which is a continuation-in-part of U.S. patent application Ser. No. 07/779,108, filed Oct. 18, 1991, now U.S. Pat. No. 5,322,503.

BACKGROUND OF THE INVENTION

1. Field of the Invention

This invention relates to a surgical instrument and more particularly to an instrument for use during laparoscopic or endoscopic surgical procedures.

2. Brief Description of the Prior Art

Laparoscopic/endoscopic surgery is a relatively new operating technique that has been developed to carry our minimally invasive surgery and more especially cholecystectomy (gallbladder removal). It can also be used in gynecology, neurosurgery, urology and other general surgical procedures.

In general, this technique is much less invasive than a conventional surgery. It involves puncturing the abdominal wall and inducing a pneumoperitoneum to distend the abdomen. A trocar of about 5 to 10 mm in diameter is inserted into the puncture and used as a guide through which one or more surgical instruments may be inserted and guided with great accuracy towards the body part requiring surgery. Such surgical instruments may include an endoscope (laparoscope), a clip applier, microscissors or forceps, an optical fiber connected to a laser source for hemostatic cutting or coagulation, a set of electrodes connected to a generator for electrocautery, etc . . . If desired, one or more smaller trocar may be inserted into the 5 to 10 mm trocar to work with two or more instruments.

Following the surgery, the puncture may be closed in a very simple manner, using a sterile suture or adhesive strip to do so. This reduces to a minimum the patient's stay at the hospital and the period for his or her recovery and resumption of normal activity. It also reduces the post-operation scar.

During surgery, it is often required to irrigate inside the abdomen with a irrigation fluid, e.g., a saline, or to suction the internal body cavity which may be, for example, the bowel or the gallbladder, without having to stop the surgical step that is being carried out. It is also required to evacuate stones or blood clots from the cavity.

Generally it is preferable to have as few punctures made in the patients' body as possible. One way of achieving this is to have both irrigation and evacuation conducted along a single conduit which, in turn, can act as an access line for surgical instruments and/or a surgical instrument itself.

A typical device which is used in laparoscopic procedures is an electrosurgical probe. Typically such a probe will comprise an radio frequency energy conductive tube covered with a dielectric material such as polyolefin or Kynar®. At one-end, for convenience called the operational end, each probe could have any one of a number of functionally shaped electrodes. In addition a probe could have its end formed specifically for irrigation and/or evacuation.

As the electrodes at the end of the probe are not necessarily symmetrical about the longitudinal axis of the probe, it is desirable for the probe to be mounted on its supporting instrument to permit rotation thereof about this axis. This would allow the manipulation of the operational end of the probe without unnecessary and inconvenient movements of the surgeon's arm. In addition, as a variety of electrode shapes are available to the surgeon it is desirable for these probes to be interchangeable.

Furthermore, any valves controlling the evacuation and irrigation procedures should be constructed so as to minimize the possibility of the valve malfunctions if, for example, any tissue or blood coagulates around their moving parts. Similarly if any of the instrumentation is to be reusable, such instrumentation, including the valves, should be capable of being efficiently sterilized or cleaned by, for example, flushing.

In many of the devices used, the irrigation fluid is supplied under pressure to the surgical instrument. This is done by providing some form of pressurizing device (e.g. a pump) between the supply reservoir, in which the irrigation fluid is stored, and the surgical instruments. This type of pressurizing device has the disadvantages of being expensive, inconvenient difficult to adjust irrigation fluid supply rates with and usually located remote from the surgeon performing the surgical procedures.

The need is, therefore, for a surgical tool which, in one way or another, meets the above requirements and overcomes the problems of the prior art.

SUMMARY OF THE INVENTION

Objects

Accordingly, it is an object of this invention to provide a surgical instrument which can be used for carrying out laparoscopic/endoscopic surgery and which is easy to hold and manipulate by the surgeon performing the operational procedures.

It is another object of this invention to provide such a surgical instrument in which the primary controls for the surgical tool are contained in the surgical instrument itself.

It is yet another object of this invention to provide for a surgical instrument which allows the surgeon to directly control the flow of irrigation fluid into the patient, from the surgical instrument itself. This surgical instrument should preferably also allow the surgeon to evacuate the patient and/or perform electro-surgical procedures on the patient.

Summary

Briefly, according to this invention a handheld surgical instrument comprises:

(i) a housing capable of being hand held and including a front end;

(ii) a surgical tool for mounting on the front end of the housing and including a conduit for irrigating or evacuating an interior portion of the body of a patient;

(iii) a reservoir for storing irrigation fluid therein and from which irrigation fluid can be supplied along the conduit to the body of the patient; and (iv) drive means mounted to the housing for acting on the fluid reservoir, whereby fluid can be moved from the reservoir, along the conduit to the body of the patient.

Preferably the fluid reservoir includes at least one resilient sidewall and the drive means acts on the resilient sidewall to cause the sidewall to deform and thereby decrease the volume of the reservoir to move the fluid from the reservoir.

Typically the surgical instrument also includes a fluid supply for supplying irrigation fluid to the reservoir.

Generally speaking the drive means acts to alternately decrease and increase the volume of the reservoir thereby alternately expelling fluid from and drawing fluid into the reservoir.

Furthermore, the surgical instrument would also include a valve for regulating the evacuation of the body of the patient and the conduit would be defined by a central bore formed in the surgical tool. Preferably the surgical tool is detachable from the housing and interchangeable for other surgical tools which may or may not be acted on by the drive means and/or other surgical tools which can be used for electro-surgical procedures.

The reservoir may be removably retained in a receiving bore formed in the housing or mounted onto the end of the surgical tool at which the tool is connected to the housing.

Advantages

This invention has the advantage that it provides for a surgical instrument which is easy to use and manipulate by the surgeon.

Another advantage of this invention is that it reduces the number of puncture in body of the patient in that it combines, in one embodiment, a surgical tool with a probe which can both be used as both a and evacuation conduit as well as for electro-surgical procedures.

Still another advantage of this invention is that the surgeon, using the surgical tool of this invention, can manipulate the rate of fluid flowing into the patient during irrigation of the patient.

A further advantage of the invention is that it provides for a surgical instrument onto which a number of different surgical tools, which are normally hand-operated, can be mounted and machine-driven.

Yet a further advantage of this invention is that the pistol-grip of the surgical tool can serve as both a mounting for a motor-driven tool as well as an attachment for a irrigation/evacuation conduit and/or an electro-surgical probe.

These and other objects and advantages of the present invention will no doubt become apparent to those skilled in the art after having read the following detailed description of the preferred embodiment which is illustrated in the several figures of the drawing.

IN THE DRAWINGS

In the following drawings:

FIG. 1 is a diagrammatic section through a semi-exploded elevation of one embodiment of the endoscopic surgical instrument of the invention;

FIG. 2 is a section through a receiving bore of the instrument illustrating one way of locating a probe in the bore;

FIG. 3 is a section through a similar receiving bore showing a different way of locating a probe in the bore;

FIG. 4 illustrates in (a)–(i) various electrostatic probe operational ends;

FIG. 5 is an exploded view of an alternative embodiment of the surgical instrument of the invention illustrating a disposable valve cartridge;

FIG. 6 is a cross section through the disposable valve cartridge illustrated in FIG. 5;

FIG. 7 is a partially sectioned view of one type of valve which can be used in the surgical instrument of the invention;

FIG. 10 shows a surgical cutting tool mounted onto the handset illustrated in FIG. 9; and FIG. 11 shows how three other types of surgical cutting tools can be mounted onto a handset similar to that in FIG. 9.

DETAILED DESCRIPTION OF PREFERRED EMBODIMENTS

Figure 8:
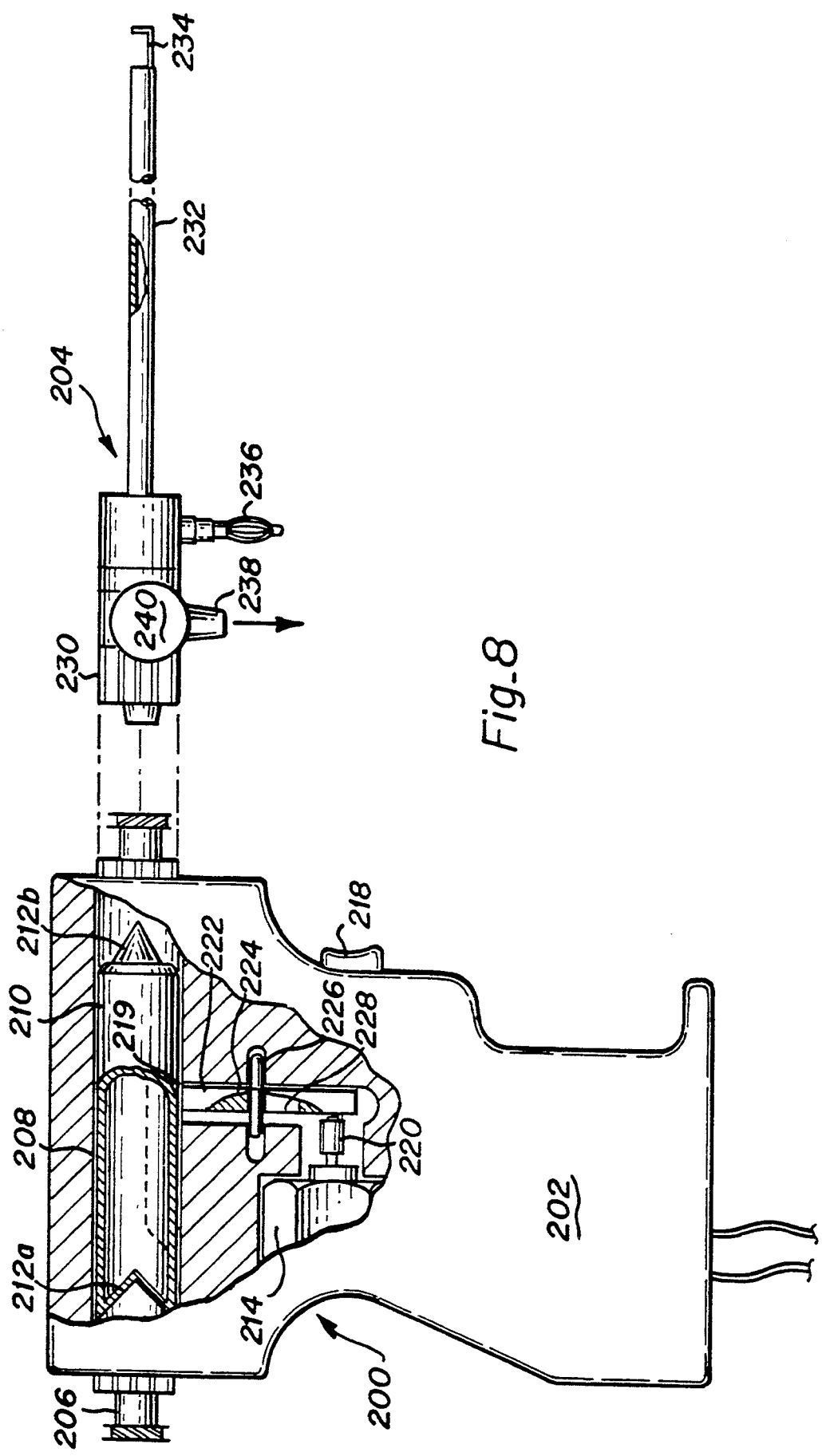
FIG. 8 is a partially sectioned, exploded view of a different embodiment of the surgical instrument of the invention illustrating a motor-driven irrigation fluid pump mounted in the handle of the instrument.

In FIG. 1 of the accompanying drawings, the endoscopic surgical instrument of the invention is generally indicated as 20. The instrument 20 is shown to include an irrigation port 21 and an evacuation port 22. Each port, 21 and 22, is connected through independent valves 23 and 24, respectively, to a single access conduit 25. The connection between the valves 23 and 24 and conduit 25 is along connector tubes 23a and 24a.

The access conduit 25 leads from the valves and their respective valve conduits to a probe connector 26. This probe connector 26 is designed to receive one end, the locating end 27, of a surgical probe 28 which would be used during microsurgical procedures. The connection 26 is described in more detail with reference to FIGS. 2 and 3 hereafter.

At or near the probe connector 26, a radio frequency connector 29 is located. As illustrated, this is in the form of a banana connector. The advantage of a banana connector is that it is an industry standard and can be used for connecting the instrument 20 to regular frequency supply sources manufactured by a number of different manufacturers.

The radio frequency connector 29 exits into the access conduit 25 where it makes connection with a point 30, on the locating end 27 of a probe 28 received by the probe connector 26.

The surgical instrument 20 also includes a port 31 which allows the surgeon to insert microsurgical instrumentation (not shown) along the access conduit 25 and the bore of the hollow probe 28 to exit from the end 32 thereof. The port 31 should provide a fluid-tight seal when no microsurgical instrumentation is being used with the surgical instrument 20. This will prevent fluid, which may be moving along the access conduit 25 to or from the patient, from leaking.

In FIG. 2 the probe connector 26 is shown to be constituted by a receiving bore which is coaxial with the fluid access conduit 25. In practice, the diameter of this bore would be the same as that of the access conduit 25 and would be sized to receive the locating end 27 of the probe 28 in a relatively close fit. Within the bore forming the probe connector, a plurality, typically two, O-rings 36 are located. When the locating end 27 is inserted into the bore 26 these O-rings provide a snug, fluid-tight seal about the end 27. Once the locating end 27 of the probe is received within the bore 26 it is capable of being rotated about its longitudinal axis, by means of a knurled rotation knob 37 located between the locating end 27 and the operational end 32 of the probe 28.

The probe 28 would typically be made of a electrostatic conductive material coated with a non-conductive material such as heat shrink polyolefin. Electrostatic/radio frequency energy is passed along the probe 28 from the radio frequency connector 29 via electrostatically conductive plates 38 located within the bore of the probe connector 26 and onto the end 30 of the probe 28. The end 30 is so designed such that when the locating end 27 of the probe is received by the probe connector 26, electrostatic connection is made between the plate 38 and the connector 30. This allows the surgeon to pass energy into the patient being operated on.

An alternative radio frequency connector is illustrated in FIG. 3. In this case, the banana connector 29 exits into the bore 26 in the form of a pin 39. In the conductive end 30 of the probe 28 an L-shaped slot 40 is formed. As the probe 28 is inserted into the receiving bore 26, the pin 39 engages the axially-orientated leg 41 of the L-shaped slot 40. When the probe can be inserted no further along the bore it is twisted, in this case in an anti-clockwise direction, such that the pin 39 and the axially transverse leg 42 of the L-shaped slot 40 engage each other to lock the probe 28 into position. In this embodiment the probe 28 cannot be rotated by means of the knurled knob 37.

FIG. 3 further illustrates an alternative positioning of the O-rings 36. In this case they are located on the locating end 27 of the probe 28.

From FIGS. 2 and 3, although not shown, it will be apparent that the diameter of the operational shank 28a of the probe 28 can be variable. Typically, the probe, as shown, would have a diameter of 5 mm. This diameter can, however, be increased to 10 mm which would be close to the diameter of the locating end 27 of the probe, as well as that of the internal bore diameter of the access conduit 25. The advantage of 10 mm diameter probes is that the evacuation of removed tissue and objects such as the gall-stones can be more effectively achieved. Obviously, when the bore of the operating shank 28a of the probe, the locating end 27 and the access conduit 25 are all 10 mm in diameter, the diameter of the evacuation port 22 and its related valve 24 and connector tube 24a must also be 10 mm.

In FIG. 4(a) to (i), a number of different electrode shapes are illustrated. These electrode tips would be located at the operating end of the probe 28.

As can be seen from the figure, a number of the tips are not symmetrical about the longitudinal access of the probe 28. It is for this reason that it is desirable for the probe 28 to be mounted on the instrument in such a manner to allow for a rotation of the probe about its longitudinal axis. This will give the surgeon the opportunity of rotating any non-symmetrical tips, inside the patient, without having to rotate his or her wrist.

It is also possible to have discardable valves for the instrument of this invention. This embodiment is illustrated in FIG. 5. In this figure the surgical instrument is shown to include a pistol grip 120, a surgical probe 122, which can be screwed into the front of the pistol grip 120 and a radio frequency connector 124 which screws into the back of the grip 120.

The instrument also includes a removable (and disposable) valve cartridge 126. The cartridge 126 includes an irrigation tube 128 and an evacuation tube 130 both of which are individually operated by valves (as will be further illustrated in FIG. 6) under action of button-shaped actuators 132. Both the irrigation and evacuation pipes communicate into a single conduit (not shown) which runs down the center of a male connector fitting 134. Where the cartridge 120 is inserted into the grip 120 the connector 134 fits into the base of a central conduit 136 which, in turn, opens up into the main access conduit 138 of the instrument. When the cartridge 120 is located in the grip 120 the actuators 132 are located directly below a pair of operating triggers 140 which can be used to operate the irrigation/evacuation procedures described before.

Finally, when the cartridge 120 is in place, it is held there by means of a retainer clip 142 which clips in behind the cartridge 120. The retainer clip 142 has apertures 144 formed in it to allow the irrigation and evacuation tubes 128, 130 to pass through it.

Although it will be apparent that many valve types would be suitable for use in the cartridge 120, one such valve configuration is illustrated in FIG. 6, which illustrates the cartridge 120 in greater detail.

In this figure, the cartridge 120 is shown to include an irrigation conduit 150 and an evacuation conduit 152, both of which lead to a central access conduit 154 which extends down the center of the male connector 134. Irrigation and evacuation procedures are controlled by irrigation and evacuation valves 156 and 158, respectively.

The irrigation valve 156 consists of a valve seal 160 mounted onto a stem which is screwed into an activator button 132a. A fluid tight seal is provided for the valve 156 by an O-ring 168 mounted onto the cap 132a. The valve seal 160 seals against a valve seat, formed at the junction between the irrigation conduit 150 and the central access conduit 154 and is held in the sealing position (as shown) by a spring 162.

Access to the valve seat is through a hole 164 formed into the top (as shown in the drawing) of the cartridge 120. This hole 164 can be closed off with a cap 166 and allows the irrigation valve 156 to be inserted into the cartridge 120. This is done by inserting the valve seal 160 and its associated stem into the hole 164 from above and inserting the spring 162 from below. Thereafter the cap 132a can be screwed onto the stem to hold the entire valve 156 in place.

To operate an irrigation procedure the button 132a is depressed to move the valve seal 160 clear of its seal to open a fluid path between the irrigation conduit and the central access conduit. Releasing the button 132a causes the spring 162 to force the seal 160 back into its seat thereby automatically shutting the valve.

The evacuation valve 158 is of a different construction. In this valve 158, the valve seal 170, in its off position as shown, seals the mouth of the evacuation conduit 152.

In operation, the seal 170 is moved under action of a plunger and evacuation button 132b from the position shown to a position 170' in which an end of a conduit 174, formed through the seal 170, aligns with the central access conduit 154. At the same time the other end of the conduit 174 is aligned with the evacuation conduit 152 and evacuation can be accomplished. By releasing the button 132b, the spring 172 biases the seal 170 back into its sealing position.

Assembly of this evacuation valve 158 is by inserting the entire valve mechanism into its valve bore and sealing a collar 176 in the bore.

As has been indicated with reference to FIG. 5, the cartridge 120 is of the disposable type and is intended for use only once. Accordingly the considerations of valve flushing (during cleaning) are not entirely applicable here.

In FIG. 7 yet one type of valve, which can be used as either an irrigation or an evacuation valve, is illustrated.

The valve, generally indicated as 180, is shown to include a hollow cylindrical valve body 182 which is sealed at its lower end by a valve seal 184 and at the other by an activator button 186. The activator button 186 seals against the valve body with an O-ring 188 and is connected to the valve seal 184 by means of a plunger 190.

To open the valve 180, the button 186 is depressed against the bias of a spring 192 to move the valve seal 184 to the position indicated in broken lines. This opens a fluid path 194 between an opening 196 formed in the sidewall of the valve body and its lower end. Releasing the button 186 allows the spring 192 to force the seal 184 back into the closed position.

One advantage of this valve is that it is very simple and cheap to manufacture and can, therefore, readily be disposed of.

Yet another embodiment of this invention is illustrated in FIG. 8. The surgical instrument, generally indicated as 200, is shown to include a pistol shaped handle 202 which has a hollow surgical tool 204 mountable at its front end. At the other end of the handle a connector 206 for connecting a source of irrigation fluid, typically saline, is located. The connector 206 communicates with the tool 204 by means of a central bore 208 located in the body of the pistol-shaped handle 202.

Inside the bore 208 a flexible pipe defining a chamber 210 is located. The chamber 210 has two one-way valves schematically shown as 212a and 212b. These one-way valves operate to allow fluid to flow in only one direction along the central bore 208 (i.e., from the connector 206 to the tool 204).

The handle 202 also includes a DC electric motor 214 powered by electric power supplied through electric cables 216 and operated by means of contact switch trigger 218. The motor 214 operates to drive an off-center cam 220 which functions to drive a plunger 222 vertically up and down (as shown in the figure) in a guide slot 224. The plunger 222 is kept in position and further guided by means of a pin 226. The pin 226 is held fixed in position relative to the handle 202 but is slidable located in a groove 228 formed in the plunger 222.

In operation the DC motor 214 drives the cam 220 to move the plunger vertically up and down. In the first half of this cycle, the plunger moves up so that its top end pushes upwards against a flat plate 219 which, in turn, bears against the wall of the chamber 210. As the walls of the chamber are flexible this causes the wall of the chamber 210 to deflect to the position indicated in broken lines. This decreases the volume of the chamber 210 forcing fluid out of the forward located one-way valve 212b. As the plunger 222 moves downwards in the second half of its cycle, the resilient side of the chamber 210 moves back to its undeformed state thereby drawing fluid in from the connector 206 through he one-way valve 218. In this way the surgeon operating the surgical instrument 200 can supply irrigation fluid along the hollow tool 204 to the patient on demand.

The tool 204 is connectable to the front of the pistol grip 202 by means of a luer lock connector 230 which provides a fluid tight connection between the tool 204 and the handle 202 but, at the same time, allows the tool 204 to be rotated about its longitudinal axis.

The tool 204 itself is shown to include a hollow polyolefin or Kynar ® coated tube 232 at the end of which a shaped tip 234 is located. The electrode tip 234 can be any suitable configuration and may even be similar to those illustrated in FIG. 4. The tool 204 also includes a radio frequency connector 236 and an evacuation port 238.

As a result of the configuration described in this figure, the surgeon can supply irrigation fluid to the patient merely by operating the trigger 218. Evacuation of the patient can be controlled by operating an evacuation button 240 which, when depressed, connects an evacuation port 238 to a source of suction (not shown). In this way, any unwanted tissue and/or irrigation fluid can be removed from the patient. In addition to providing a source of irrigation fluid and a means for evacuating the patient, the instrument 200 illustrated in this figure also, by means of the electrode tip 234, allows the surgeon to conduct other surgical procedures.

One advantage of the surgical instrument shown in this figure, is that the chamber 210 is in the form of a cartridge which can easily be removed by unscrewing the connector 206 and sliding the cartridge out of the bore 208. Alternatively, the connector 206 and the chamber 210 can be joined together so that they can jointly be inserted into the bore 208. In this configuration the housing 202 could include a clip (not shown) that clips over the connector 206 to hold it in place. This means that the cartridge can be removed and replaced when worn, or, to ensure maximum sterile operating conditions, after each surgical procedure.

Figure 9:
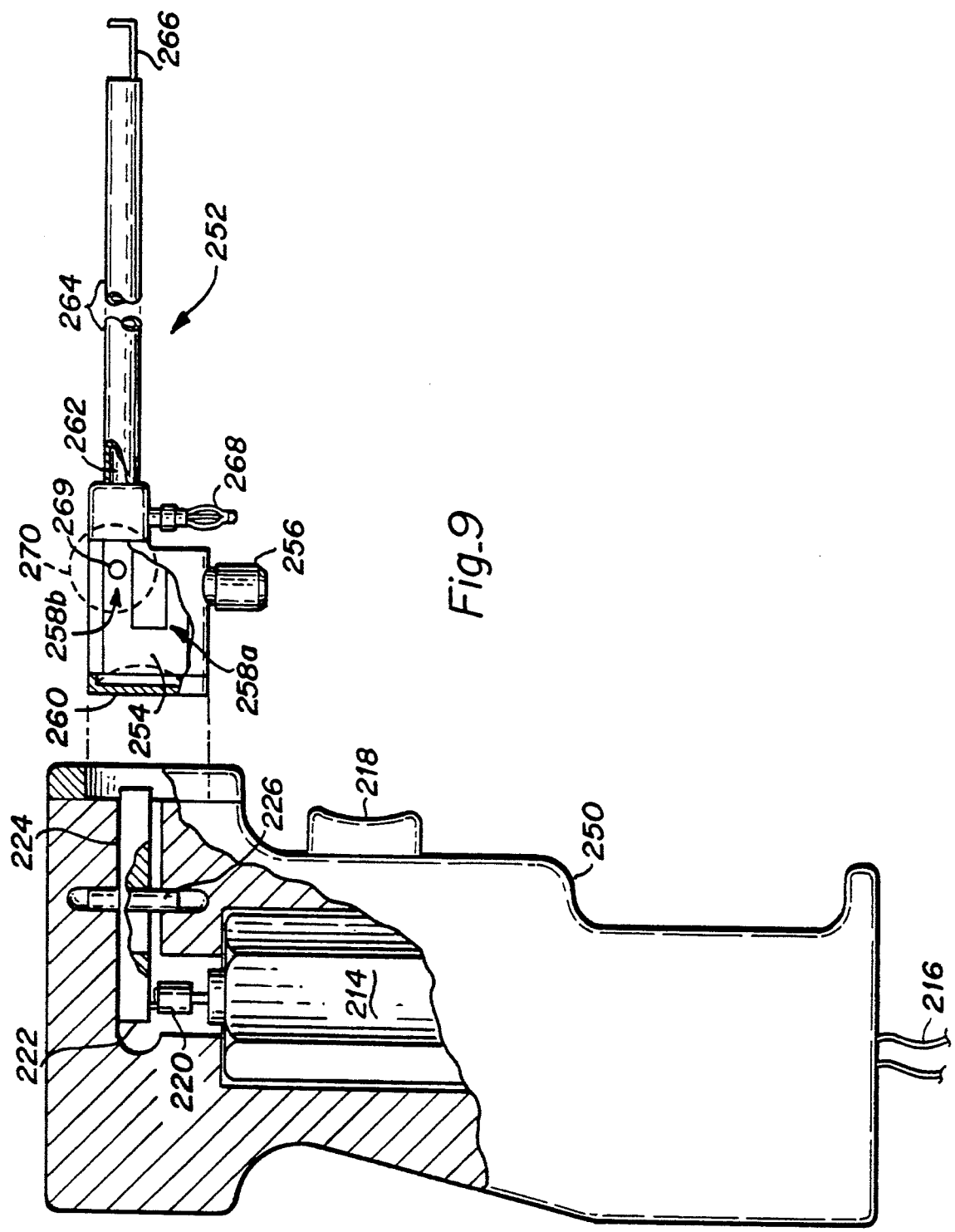
FIG. 9 is yet a different embodiment of the invention, illustrating an alternative motor-driven irrigation fluid pump.

In FIG. 9 an alternative embodiment of the motor-drive hand held surgical instrument is generally illustrated as 250. In this figure components similar, or operating in a similar fashion, to those in FIG. 8 are given the same reference numerals. Accordingly, this figure shows a DC motor 214 which has power supplied to it via cables 216 and is operable by means of a contact switch trigger 218. In a manner similar to that in FIG. 8 the DC motor 214 drives a plunger 222 in a guide slot 224.

In this embodiment, however, a tool 252, which is shown to be connectable to the front end of the instrument 250, includes a pump means which defines a fluid chamber 254. The fluid is supplied to this chamber 254 via a fluid inlet port 256 and is forced to flow in a direction from the port 256 towards the front end of the tool 252 by means of two one-way valves 258a, 258b.

Fluid is forced out of and drawn into the chamber 254 under action of the plunger 222. As the plunger 222 moves laterally in the slot 224, it alternatively contacts (and deforms) and releases a flexible and resilient diaphragm 260 which forms one of the outer walls of the chamber 254. During this cycle the diaphragm 260 moves between its distorted position (shown in broken lines) and its natural, undistorted position. In doing so the volume in the chamber 254 alternately increases and decreases thereby alternately drawing fluid into the chamber through valve 258a and forcing it out through valve 258b. As the fluid is forced out of the chamber 254 it flows through a valve 258b along the central bore 262 of a conduit 264.

As with the example in FIG. 8 the conduit 264 has an electrode tip 266 which can take on many different forms and shapes. Radio frequency is supplied to this operational end 266 via a radio frequency connector in the form of a banana plug 268.

Evacuation of the patient can be achieved via the central bore 262 of the conduit 264 and an evacuation port 269 controlled by a valve (not shown) and an evacuation control button 270 shown superimposed in broken lines on the figure.

FIG. 10 shows a different use for the instrument 250 Of FIG. 9. The handle in this figure is identical to the handle illustrated in FIG. 9 except that the front of the plunger 222 has a ball-shaped socket 280 formed therein. This socket 280 is sized to receive, under a force fit, a complimentally sized and shaped ball fitting 282. The ball 282 forms part of a generally hollow inner cannula which has a hollow cutting element 284 formed at its end opposite from the all 282. The inner cannula 286 is, itself, located within an outer cannula 288 at the operational end of which, a semicircular cutout 290 is formed.

During operation, the plunger 222 forces the internal conduit 286 to move laterally along the bore of the outer cannula 288. As a result, the cutting element 284 moves from the position shown to that indicated in broken lines. This results in a cutting action between the front edge of the cutter 284 and the inner edge of the semicircular cutout 290. Accordingly, any tissue which has been located by the surgeon in the semicircular cutout 290 will be cut off and can be removed from the patient. This is done by applying a suction at an evacuation port 292. Next to the evacuation port 292, an irrigation port 293 is also shown. This port is connected to a source of irrigation fluid (not shown) and is controlled by means of button 294. The button 294 regulates a valve which can selectively open/close both ports so as to regulate evacuation/irrigation of the patient. The evacuation/irrigation ports 292, 293 communicate with the interior of the inner cannula 286 by means of a number of slots 296 formed in the sidewall thereof.

FIG. 11 shows 3 different types of cutting tools which can be mounted onto the handle 250 of this invention. As can be seen, each of these cutting instruments operates under a lateral force being applied to their respective operational ends by means of a rod 300 which is connected directly to the ball 282 located at the opposite end of the surgical tool 302 in question. As the rod 300 moves up and down within a probe 304 it forces a lattice linkage 306 to open and close thereby forcing the cutting instrument 310 at the end of the probe to open and close as well.

An important feature of this invention is that the irrigation and evacuation tool 252 illustrated in FIG. 9 is interchangeable with the tools 288 and 302 in FIGS. 10 and 11. This allows the surgeon to have only one handle which he can use with any one of a number of different operational tools.

In addition, the embodiment described in FIG. 8 to 11 are driven by means of a DC motor. The speed of this DC motor can be varied by providing differing amounts of voltage to the DC motor. This can be achieved by providing a voltage regulator between the power source and the tool or, alternatively, having a variable resistor behind the trigger 218 so that different pressure on the trigger 218 result in different speeds of the DC motor and therefore different cutting speeds and/or irrigation flow rate.

Finally, it will be apparent to anyone skilled in the art, that the surgical instrument of this invention could be made from any suitable material. In the event that the instrument is intended for use only once, some form of plastic material could be used. Alternatively, for repetitive use of the instrument, the instrument can be made of a more durable material such as aluminum, stainless steel, etc.

Although the present invention has been described above in terms of a specific embodiment, it is anticipated that alterations and modifications thereof will no doubt become apparent to those skilled in the art. It is therefore intended that the following claims be interpreted as covering all such alterations and modifications as fall within the true spirit and scope of the invention.

What is claimed is:

1. A handheld surgical instrument comprising:
   (i) a housing capable of being hand held and including a front end;
   (ii) a first connector formed in the housing and adapted for communicating with a source of fluid;
   (iii) a second connector formed in the front end of the housing;
   (iv) an elongated surgical tool removably attached to the second connector and including a conduit axially formed within said tool and adapted for communicating with the second connector, the conduit being based for irrigating and evacuating an interior portion of the body of a patient;
   (v) an elongated chamber disposed within the housing and having a distal end and a proximal end, the distal end being in communication with the second connector and the proximal end being in communication with the first connector, the chamber having at least one sidewall resiliently deflectable between a first undeflected state and a second deflected state;
   (vi) drive means disposed within the housing for alternatingly engaging with and disengaging from the sidewall of the chamber such that when the drive means is engaged with the sidewall the sidewall is in the second state and when the drive means is disengaged from the sidewall, the sidewall is in the first state whereby, when the source is in communication with the first connector and the conduit is in communication with the second connector, disengaging the drive means from the sidewall increases the volume of the chamber thereby drawing fluid into the chamber from the source, and engaging the drive means with the sidewal decreases the volume of the chamber thereby expelling fluid therefrom and into the conduit and the fluid is moved from the source, along the conduit to irrigate the body of the patient.

2. A handheld surgical instrument according to claim 1, wherein the chamber includes at least one one-way valve to ensure that the direction of fluid movement is from the chamber to the patient, said one-way valve being disposed at either said distal end or said proximal end of said chamber.

3. A handheld surgical instrument according to claim 2, wherein the drive means includes a plunger restrained to reciprocate within the housing to act on the sidewall of the chamber.

4. A handheld surgical instrument according to claim 3, further comprising an evacuation valve disposed in the conduit and adapted for communicating with a receiver of fluid, said evacuation valve being positionable between a first position and a second position such that in said first position fluid is blocked from said receiver and the chamber is in communication with a body cavity of the patient, and in said second position fluid is blocked from the chamber and the body cavity of the patient is in communication with said receiver of fluid.

5. A handheld surgical instrument according to claim 4, wherein the conduit is a bore formed in the surgical tool.

6. A handheld surgical instrument according to claim 5, wherein the housing includes a receiving bore and the chamber is defined by a cartridge which is removably retained in the receiving bore.

7. A handheld surgical instrument according to claim 5, wherein the surgical tool includes an operational tip at the end of the conduit for insertion into the body of the patient and a connecting end for connection to the housing and wherein the chamber is located at the connecting end of the tool.

8. A handheld surgical instrument according to claim 7, wherein the drive means further includes an electric motor which operates to reciprocate the plunger laterally within the housing.

9. A handheld surgical instrument comprising:
   (i) a housing capable of being hand held and including a front end;
   (ii) an elongated surgical tool including a free end for insertion into the body of a patient and a secure end removably attached to the front end of the housing;
   (iii) a conduit formed within and aligned along the longitudinal axis of the surgical tool, for irrigating and evacuating an interior portion of the body of a patient;
   (iv) a chamber disposed within and adjacent to the secure end of the surgical tool and in communication with the conduit, the chamber having at least one resilient wall that is deflectable between a first undeflected state and a second deflected state;
   (v) a first connector formed in a wall of the chamber and adapted for communicating with a fluid source;
   (vi) drive means disposed within the housing for alternatingly engaging with and disengaging from the resilient wall of the chamber when the tool is attached to the front end, such that when the drive means is engaged with the resilient wall the resilient wall is in the second state, and when the drive means is disengaged from the resilient wall the resilient wall is in the first state;
   (vii) whereby disengaging the drive means from the resilient wall increases the volume of the chamber thereby drawing fluid into the chamber from the fluid Source, and engaging the drive means with the resilient wall decreases the volume of the chamber thereby expelling fluid therefrom into the conduit and into the body cavity of the patient.

10. A handheld surgical instrument according to claim 9, further comprising an evacuation valve disposed in the conduit and adapted for communicating with a receiver of fluid, said evacuation valve being positionable between a first position and a second position such that in said first position fluid is blocked from said receiver and the chamber is in communication with a body cavity of the patient, and in said second position fluid is blocked from the chamber and the body cavity of the patient is in communication with said receiver of fluid.

11. A handheld surgical instrument according to claim 10, wherein the drive means includes a plunger restrained to reciprocatingly engage the resilient wall of the chamber.

* * * * *